United States Patent
Goldberg

(10) Patent No.: US 11,653,993 B2
(45) Date of Patent: May 23, 2023

(54) COMPARTMENTALIZED MEDICAL SURGICAL KIT SYSTEM

(71) Applicant: Grigory Goldberg, Belle Meade, NJ (US)

(72) Inventor: Grigory Goldberg, Belle Meade, NJ (US)

( * ) Notice: Subject to any disclaimer, the term of this patent is extended or adjusted under 35 U.S.C. 154(b) by 120 days.

(21) Appl. No.: 16/948,440

(22) Filed: Sep. 18, 2020

(65) Prior Publication Data
US 2021/0077215 A1 Mar. 18, 2021

Related U.S. Application Data

(60) Provisional application No. 62/902,026, filed on Sep. 18, 2019.

(51) Int. Cl.
*A61B 50/30* (2016.01)
*A61B 50/00* (2016.01)

(52) U.S. Cl.
CPC ........ *A61B 50/30* (2016.02); *A61B 2050/002* (2016.02); *A61B 2050/0079* (2016.02); *A61B 2050/0085* (2016.02); *A61B 2050/3008* (2016.02)

(58) Field of Classification Search
CPC .............. A61B 50/30; A61B 2050/002; A61B 2050/3008
USPC .................................................. 206/363, 370
See application file for complete search history.

(56) References Cited

U.S. PATENT DOCUMENTS

| | | | | |
|---|---|---|---|---|
| 3,343,669 A * | 9/1967 | Loran | ..................... | A61C 19/02 206/63.5 |
| 4,501,363 A * | 2/1985 | Isbey, Jr. | ................ | A61B 50/33 206/363 |
| 5,598,921 A * | 2/1997 | Hunt | ..................... | B43M 99/008 206/214 |
| 5,791,472 A * | 8/1998 | Davis | ..................... | A61B 50/33 220/756 |
| 5,848,693 A * | 12/1998 | Davis | ..................... | A61B 50/33 206/370 |
| 6,158,437 A * | 12/2000 | Vagley | .................. | A61C 19/02 206/439 |
| 2003/0118491 A1* | 6/2003 | Frieze | ....................... | A61L 2/26 422/292 |
| 2006/0243682 A1* | 11/2006 | Wang | .................... | G06F 1/1601 211/59.1 |

(Continued)

OTHER PUBLICATIONS

"3M Steri-Drape Instrument Pouch—1018, 3M Model: 1018," MedexSupply.com, Dec. 13, 2021, https://www.medexsupply.com/surgical-supplies-surgical-drapes-3m-steri-drape-instrument-pouch-1018-x_pid-2110.html?pid=2110&gclid=Cj0KCQiAqbyNBhC2ARIsALDwAsA4x-C5virsnvtR55dY6p6nuEsbcA5v_J8rrLPCAQZUZkmoumnO1UQaAkTKEALw_wcB (2 pages).

(Continued)

*Primary Examiner* — Steven A. Reynolds

(74) *Attorney, Agent, or Firm* — Fox Rothschild LLP

(57) ABSTRACT

A compartmentalized medical instrument kit is provided. The compartmentalized medical instrument kit includes a platform configured for use during medical procedures. The platform may include a top surface, a plurality of sidewalls, and/or a bottom surface, wherein the bottom surface includes one or more channels configured to receive one or more wires and to secure and position the one or more wires under the platform. The compartmentalized medical instrument kit may include one or more compartments configured to house one or more medical instruments.

20 Claims, 4 Drawing Sheets

(56) References Cited

U.S. PATENT DOCUMENTS

| | | | | |
|---|---|---|---|---|
| 2008/0202976 A1* | 8/2008 | Burgess | ............... | A47B 88/994 |
| | | | | 206/557 |
| 2009/0260284 A1* | 10/2009 | Barbalho | ............... | A01G 9/033 |
| | | | | 47/65.9 |
| 2010/0243844 A1* | 9/2010 | Peloza | .................... | A61B 5/03 |
| | | | | 248/310 |
| 2016/0136352 A1* | 5/2016 | Smith | ................... | A61M 5/008 |
| | | | | 206/366 |
| 2017/0156811 A1* | 6/2017 | Cerda | .................... | B65B 55/04 |
| 2017/0224435 A1* | 8/2017 | Godfrey | ................. | A61B 50/33 |
| 2017/0295275 A1* | 10/2017 | Houtchens | ............. | H04M 1/62 |

OTHER PUBLICATIONS

"Covidien 31140570 Magnetic Drape, 10" x 16"-30/cs," Tiger Medical, Inc., Dec. 13, 2021, https://www.tigermedical.com/Products/Magnetic-Drape—10-x-16—30cs_COV31140570.aspx?invsrc=adwords_tm&gclid=Cj0KCQiAqbyNBhC2ARIsALDwAsBh3X6tMSFE7_eZR_qZoyHCCR0Php9Ob_nDOmao6Ja4eyFeamjooiwaAsH1EALw_wcB (1 page).

* cited by examiner

COMPARTMENTALIZED MEDICAL SURGICAL KIT SYSTEM

CROSS-REFERENCE TO RELATED APPLICATIONS

This application claims priority under 35 U.S.C. § 119(e) to U.S. Provisional Application No. 62/902,026, filed Sep. 18, 2019, the disclosure of which is incorporated herein by reference in its entirety.

TECHNICAL FIELD

The present disclosure relates to medical instrument holders and, in particular, to compartmentalized medical instrument kit systems for safely and efficiently storing medical equipment on or near a patient while organizing one or more wires necessary for medical equipment.

BACKGROUND

When analyzing a patient or performing a simple or complex medical procedure on a patient, medical professionals are typically not merely using their hands. They are often using various types of physical medical instruments. These medical instruments and, in particular, handheld medical instruments, play important roles in the facilitation of many medical procedures, especially surgical procedures, each having one or more specific functions during the medical procedure or procedures and many being necessary for successful treatment or diagnosis.

As advancements in medicine continue to progress, so does the advancement and development of handheld medical instruments, leading to the ever growing importance of their use in medical procedures and their organization and ease of access during medical procedures. However, the standard means by which these medical instruments are presented to medical professionals during medical procedures includes presenting the medical instruments on a platform, such as a table, separate and apart from the patient and the medical table. This separates the medical professional from the medical instruments during the medical procedure when the medical professional should have access to all of the necessary medical instruments while still having access to the patent.

Additionally, the ever growing complexities of medical instruments, including their multiple parts and the addition of any necessary tubes or wires, necessitates having the ability to organize and secure the medical instruments during the medical procedures.

For at least these reasons, a system for organizing medical instruments while simultaneously presenting the medical instruments to the medical professional for easy access while the medical professional is accessing the patient is needed.

SUMMARY

According to an aspect of the present disclosure, a compartmentalized medical instrument kit is provided. The compartmentalized medical instrument kit includes a platform configured for use during medical procedures. The platform may include a top surface, a plurality of sidewalls, and/or a bottom surface, wherein the bottom surface includes one or more channels configured to receive one or more wires and to secure and position the one or more wires under the platform. The compartmentalized medical instrument kit may include one or more compartments configured to house one or more medical instruments.

In some embodiments, one or more of the one or more compartments are coupled to one or more of the plurality of sidewalls. In some embodiments, one or more of the one or more compartments are coupled to the top surface. In some embodiments, the one or more compartments are romovably coupled to the platform and configured to be positioned at multiple location points on the platform.

In some embodiments, the platform is configured to be positioned over a portion of a patient during a medical procedure.

In some embodiments, the platform is flexible. In some embodiments, the platform is rigid.

In some embodiments, the one or more compartments include one or more dividers configured to separate each of the one or more compartments into a plurality of pockets.

In some embodiments, the bottom surface further includes a securing mechanism configured to secure the bottom portion of the platform to a surface.

In some embodiments, the securing mechanism is selected from the group consisting of a hook and loop fastener, an adhesive, and a magnet.

In some embodiments, the one or more compartments include one or more materials selected from the group consisting of plastic, metal, and rubber.

In some embodiments, the compartmentalized medical instrument kit further includes one or more medical instrument securing mechanisms.

In some embodiments, the one or more medical instrument securing mechanisms are selected from the group consisting of one or more hooks, one or more clips, one or more adhesive components, and one or more hook and loop fasteners.

In some embodiments, one or more of the one or more medical instrument securing mechanisms are coupled to one or more surfaces selected from the group consisting of one or more of the one or more sidewalls and the top surface. In some embodiments, the one or more medical instrument securing mechanisms are romovably coupled to the platform and configured to be positioned at multiple location points on the platform.

In some embodiments, the platform includes one or more materials selected from the group consisting of metal, plastic, and rubber.

In some embodiments, the top surface includes a non-slip surface, aiding in the prevention of any medical instruments from sliding off of the top surface during the commencement of a medical procedure.

DETAILED DESCRIPTION

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

Figure 1:
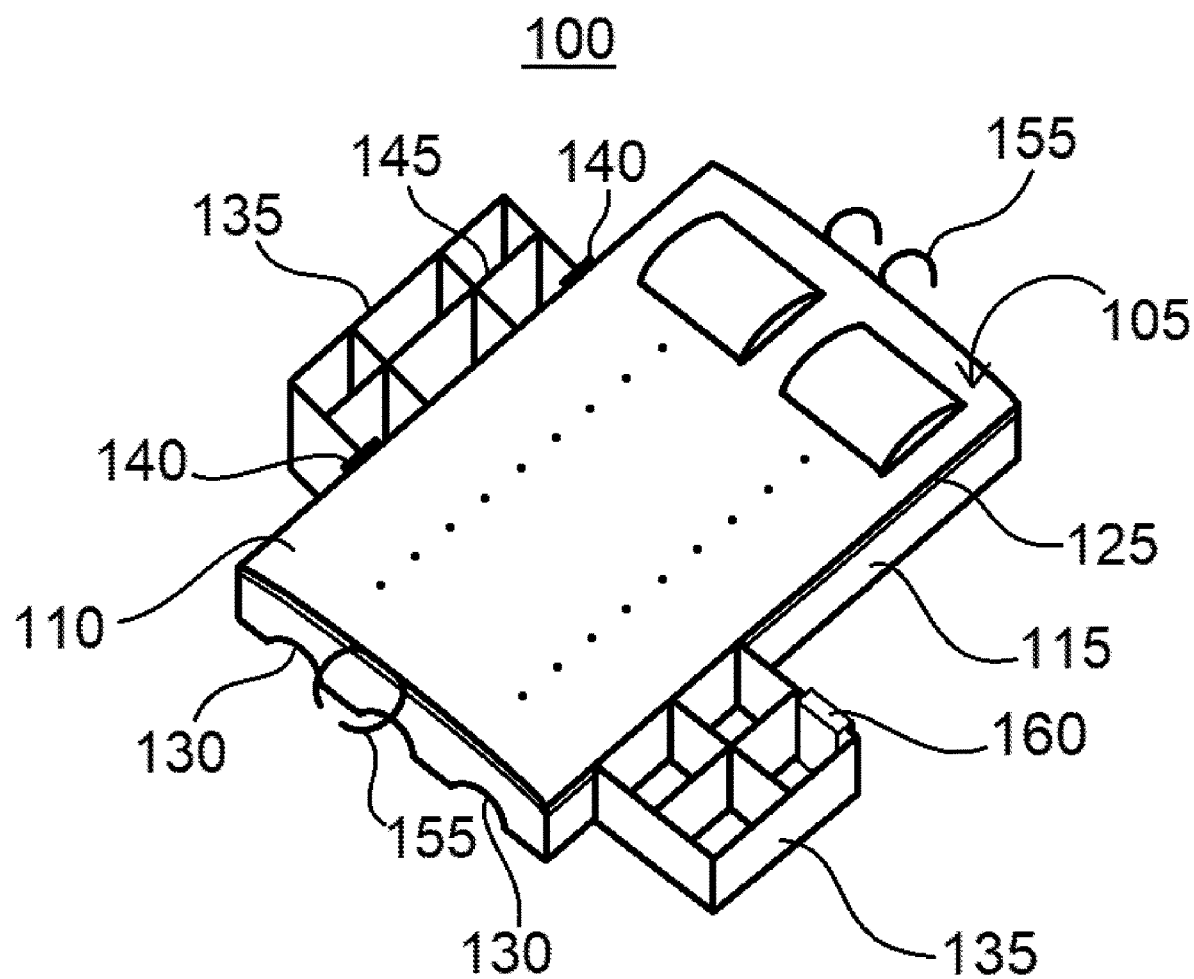
FIG. 1 is a perspective view of an example of a compartmentalized medical instrument kit system of the present disclosure.
Figure 2:
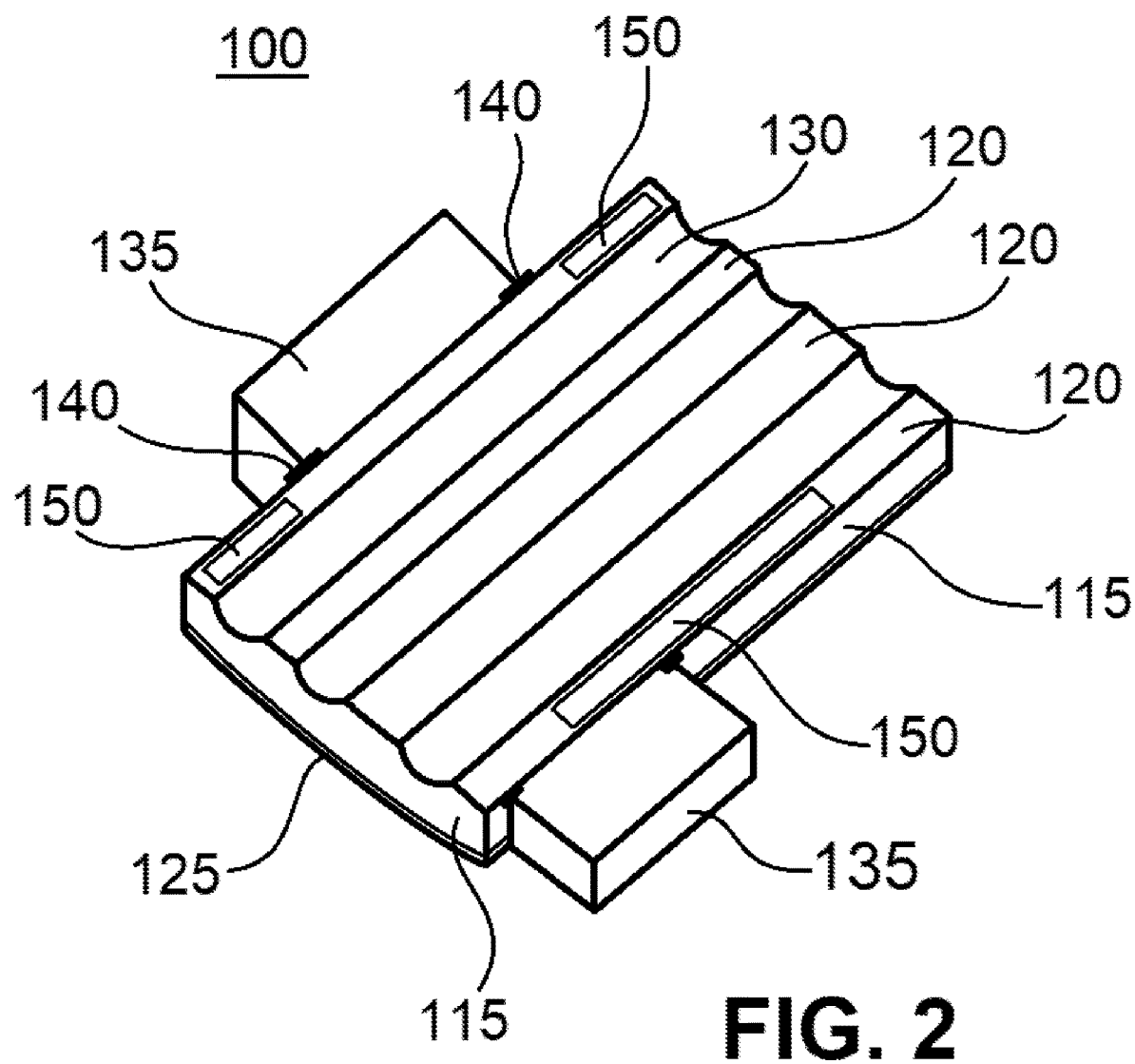
FIG. 2 is a bottom view of an example of a compartmentalized medical instrument kit system of the present disclosure.

Referring now to FIGS. 1-2, a perspective view (FIG. 1) and a bottom view (FIG. 2) of a compartmentalized medical instrument kit system 100 are illustratively depicted in accordance with various embodiments presented in the present disclosure.

According to various embodiments, the compartmentalized medical instrument kit system 100 is configured to be placed or positioned on a portion of a patient or a medical table during a medical procedure conducted by a medical professional. This grants the medical professional access to any medical instruments housed within the compartmentalized medical instrument kit system 100 during the medical procedure, while organizing the plurality of medical instruments for ease of access, thus facilitating the safe commencement of the medical procedure and thus also improving upon existing technologies for storing medical instruments during medical procedures.

The compartmentalized medical instrument kit system 100 may include a platform 105. The platform 105 may, according to various embodiments, be rigid, may have some degree of flexibility, and/or may have some degree of rigidity and flexibility. The platform 105 includes a top surface 110, a plurality of sidewalls 115, and a bottom surface 120. The platform 105 may include materials such as, for example, plastic, metal, rubber, glass, and/or any other suitable material.

While the compartmentalized medical instrument kit system 100 is in use during a medical procedure, the top surface 110 is positioned such that a medical profession can place one or more medical instruments upon the top surface 110. According to various embodiments, the top surface 110, being configured for the placement of one or more medical instruments, includes a non-slip texture and/or material 125, aiding in the prevention of any medical instruments from sliding off of the top surface 110 of the platform 105 during the commencement of a medical procedure, aiding in the safe using of the compartmentalized medical instrument kit system 100.

There are many different types of medical instruments, having many different shapes and sizes. Many medical instruments are non-electric, have no hoses or tubes attached, have an internal power source (eliminating the need for a wired power source), and/or communicate data wirelessly (eliminating the need for a wired connection to one or more secondary electronic devices). However, many medical instruments include various wires, cords, tubes, etc. coupled to the handheld portion of the medical instruments. When using these types of medical instruments, in order to maintain a safe and organized space to conduct the medical procedure, it is important to secure and house these extraneous components of the medical instruments.

According to various embodiments, the bottom surface 120 of the platform 105 may include one or more channels 130. These channels 130 are configured to receive one or more wires, cords, communication channels, tubes, and/or any other suitable components and position and secure these components under the platform 150 during the commencement of a medical procedure. These channels 130 thus aid in the organization of the components of medical instruments during medical procedures, thus providing increased safety in the use of the medical instruments.

The bottom surface 120 of the platform 105 is configured to rest on a surface such as, e.g., a portion of a patient, a medical/surgical table, and/or any other suitable surface. According to various embodiments, the bottom surface 120 of the platform 105 is secured to the surface via one or more securing mechanisms 150. The one or more securing mechanisms 150 may include a hook and loop fastener, an adhesive, a magnet, and/or any other suitable form of securing mechanism 150.

According to various embodiments, the compartmentalized medical instrument kit system 100 may be configured to store one or more surgical instruments while in use during a medical procedure. The compartmentalized medical instrument kit system 100 may include one or more storage compartments 135 coupled to the platform 105, the one or more storage compartments being configured to store one or more medical instruments. The one or more compartments may include materials such as plastic, metal, rubber, and/or any other suitable materials.

The one or more storage compartments 135 may be coupled to one or more of the plurality of sidewalls 115 of the platform 105. One or more of the one or more storage compartments 135 may be permanently affixed to one or more of the plurality of sidewalls 115 (either as one single piece or via the permanent affixing of two or more separate pieces) and/or may be removably coupled to one or more of the plurality of sidewalls 115, enabling the one or more storage compartments 135 to be moved from one section of the platform 105 to another section of the platform 105. Alternatively, or in addition, the one or more storage compartments 135 may be coupled to the top surface 110 of the platform 105. According to various embodiments, the one or more storage compartments 135 may be configured to be repositioned at various locations on the platform 105. Each side (including the top, bottom, and/or one or more of the sidewalls) of the compartmentalized medical instrument kit system 100 may include one or more storage compartments 135 and/or one or more securing mechanisms 155.

The one or more compartments 135 may be coupled to the platform 105 via one or more securing mechanisms 140. These one or more securing mechanisms 140 may include an adhesive, a snap fastener, hook and loop fasteners, a magnet, and/or any other suitable form of securing mechanism 140.

Figure 4:
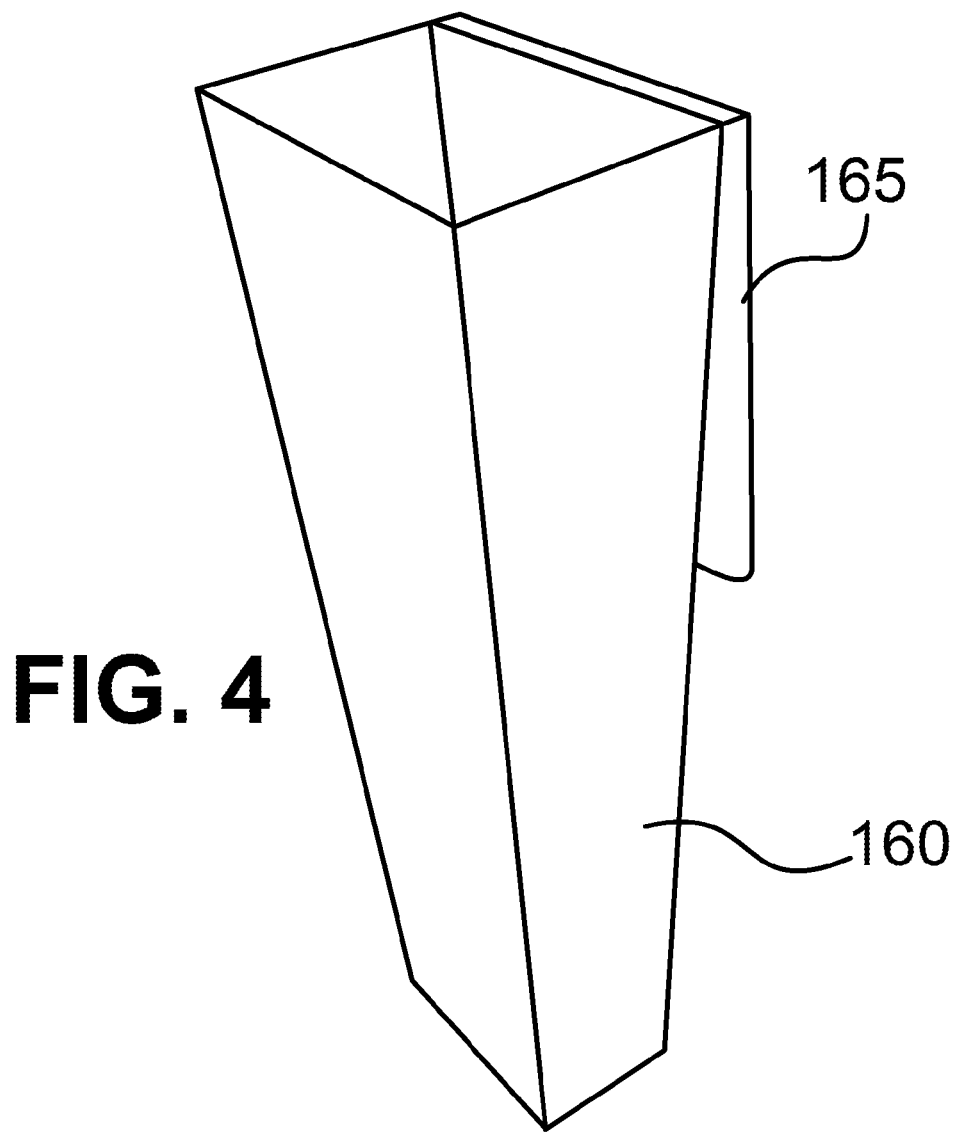
FIG. 4 is a perspective view of an example of an insert configured to be inserted into one or more compartments.

According to various embodiments, the one or more compartments 135 may be single compartments or may include one or more dividers 145 positioned within the one or more compartments. These one or more dividers 145 are positioned with the one or more compartments 135, dividing each of the one or more compartments 135 into a plurality of sections for storing one or more medical instruments, enabling the medical professional to adequately and safely organize the medical instruments while the compartmentalized medical instrument kit system 100 is in use. According to various embodiments, one or more inserts 160 (shown in more detail in FIG. 4) may be inserted into the one or more compartments 135. The one or more inserts 160 may include a retaining mechanism for retaining the position of the insert 160 within the compartment 135. The insert 160 may include plastic, metal, and/or any other suitable material. According to various embodiments, the insert 160 may be subdivided into two or more subcompartments.

According to various embodiments, the compartmentalized medical instrument kit system 100 may further include one or more securing mechanisms 155 configured to secure one or more medical instruments to the platform 105. The one or more securing mechanisms 155 may include, e.g., one or more hooks, one or more clips, one or more adhesive components (e.g., an adhesive strip), one or more hook and loop fasteners, and/or any other suitable form of securing mechanism 155 for securing one or more medical instruments to the platform 105. One or more of the one or more securing mechanisms may be coupled to any of the plurality of sidewalls 115 and/or the top surface 110. One or more of the one or more securing mechanisms 155 may be permanently coupled to the platform 105 and/or may be removably coupled to the platform 105. According to various embodiments, the one or more securing mechanisms 155 may be able to be repositioned on the platform 105.

Figure 3:
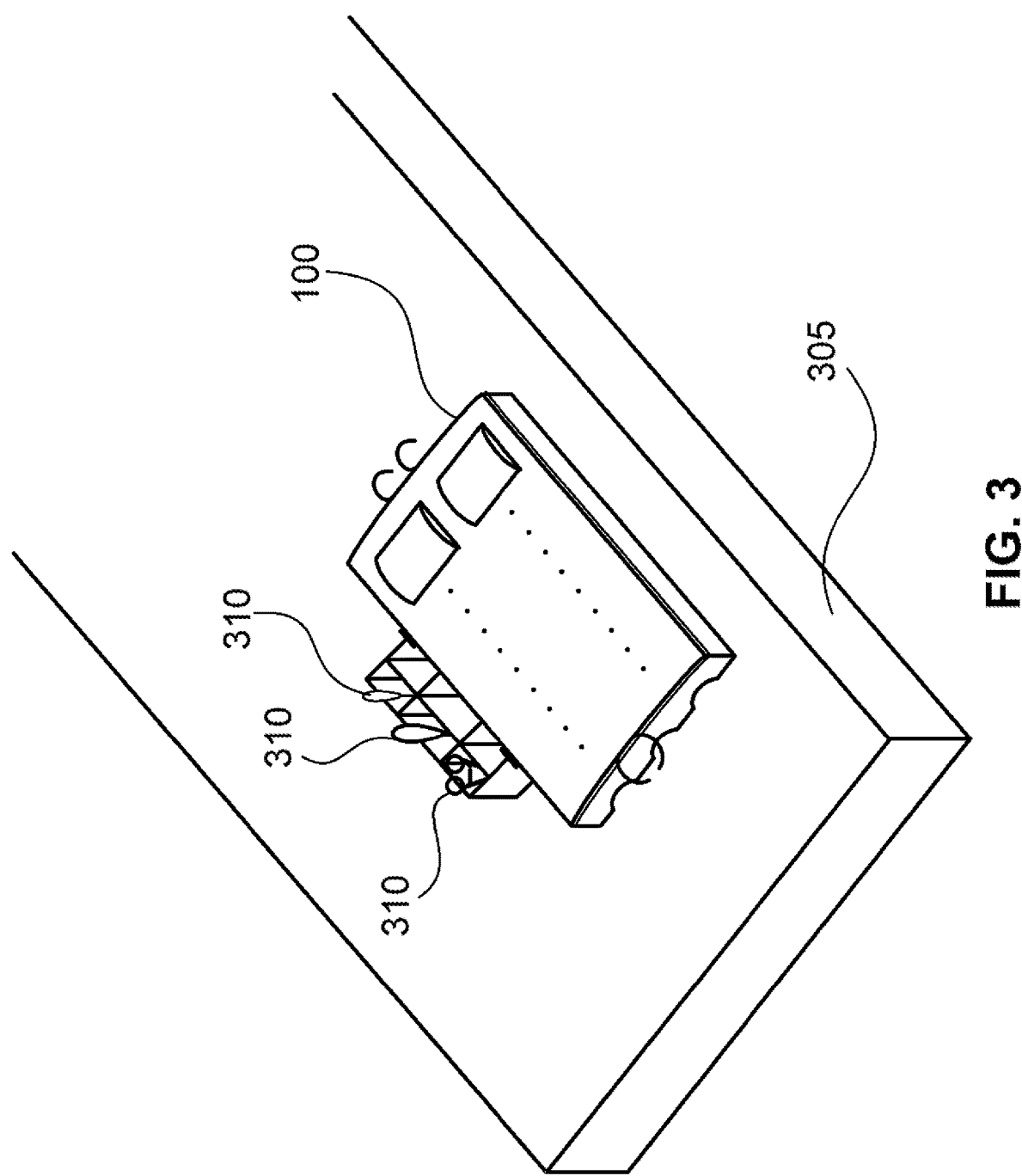
FIG. 3 is a diagram of an example a compartmentalized medical instrument kit system of the present disclosure in use during a medical procedure.

Referring now to FIG. 3, a diagram of an example a compartmentalized medical instrument kit system 100 positioned on a surgical table 305 such as during a medical procedure is illustratively depicted.

As shown in FIG. 3, the compartmentalized medical instrument kit system 100 may be positioned on a portion of a surgical table 305 or bed, and/or may be positioned directly over a portion of a patient. The compartmentalized medical instrument kit system 100 houses a plurality of medical instruments 310. The compartmentalized medical instrument kit system 100 is positioned such that a medical professional, while performing a medical procedure, is able to organize and access the one or more medical instruments 310, facilitating the safe and successful completion of the medical procedure.

While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

What is claimed is:

1. A compartmentalized medical instrument kit comprising:
  a platform configured for use during medical procedures, the platform including:
    a generally flat top surface;
    a plurality of sidewalls extending downward from the top surface; and
    a bottom surface,
  wherein:
    the bottom surface includes one or more channels configured to receive one or more wires and to secure and position the one or more wires under the platform,
    the one or more channels have a shape complimentary to a shape of the one or more wires, and
    the one or more channels extend entirely along the bottom surface, from one end of the bottom surface to another end of the bottom surface; and
  one or more compartments configured to house one or more medical instruments,
    wherein the one or more compartments are coupled to the platform and are positioned external to the top surface and the plurality of sidewalls.

2. The compartmentalized medical instrument kit as recited in claim 1, wherein one or more of the one or more compartments are coupled to one or more of the plurality of sidewalls.

3. The compartmentalized medical instrument kit as recited in claim 1, wherein one or more of the one or more compartments are coupled to the top surface.

4. The compartmentalized medical instrument kit as recited in claim 1, wherein the one or more compartments are removably coupled to the platform and configured to be positioned at multiple location points on the platform.

5. The compartmentalized medical instrument kit as recited in claim 1, wherein the platform is configured to be positioned over a portion of a patient during a medical procedure.

6. The compartmentalized medical instrument kit as recited in claim 1, wherein the platform is flexible.

7. The compartmentalized medical instrument kit as recited in claim 1, wherein the platform is rigid.

8. The compartmentalized medical instrument kit as recited in claim 1, wherein the one or more compartments include one or more dividers configured to separate each of the one or more compartments into a plurality of pockets.

9. The compartmentalized medical instrument kit as recited in claim 1, wherein the bottom surface further includes a securing mechanism configured to secure the bottom portion of the platform to a surface.

10. The compartmentalized medical instrument kit as recited in claim 9, wherein the securing mechanism is selected from the group consisting of a hook and loop fastener, an adhesive, and a magnet.

11. The compartmentalized medical instrument kit as recited in claim 1, wherein the one or more compartments include one or more materials selected from the group consisting of plastic, metal, and rubber.

12. The compartmentalized medical instrument kit as recited in claim 1, further comprising:
  one or more medical instrument securing mechanisms.

13. The compartmentalized medical instrument kit as recited in claim 12, wherein the one or more medical instrument securing mechanisms are selected from the group consisting of one or more hooks, one or more clips, one or more adhesive components, and one or more hook and loop fasteners.

14. The compartmentalized medical instrument kit as recited in claim 12, wherein one or more of the one or more medical instrument securing mechanisms are coupled to one or more surfaces selected from the group consisting of:
  one or more of the one or more sidewalls; and
  the top surface.

15. The compartmentalized medical instrument kit as recited in claim 12, wherein the one or more medical instrument securing mechanisms are removably coupled to the platform and configured to be positioned at multiple location points on the platform.

16. The compartmentalized medical instrument kit as recited in claim 1, wherein the platform includes one or more materials selected from the group consisting of metal, plastic, and rubber.

17. The compartmentalized medical instrument kit as recited in claim 1, wherein the top surface further includes a non-slip material.

18. The compartmentalized medical instrument kit as recited in claim 1, further comprising one or more securing mechanisms,
    wherein the one or more compartments are coupled to the platform via the one or more securing mechanisms.

19. The compartmentalized medical instrument kit as recited in claim 18, wherein the one or more securing mechanisms comprise at least one of the following:
    an adhesive;
    a snap fastener;
    a hook and loop fastener; and
    a magnet.

20. The compartmentalized medical instrument kit as recited in claim 1, further comprising one or more inserts configured to be inserted within the one or more compartments,
    wherein each insert of the one or more inserts comprises a retaining mechanism configured to retain a position of the insert within the one or more compartments.

\* \* \* \* \*